United States Patent [19]

Schramm et al.

[11] Patent Number: 5,301,539

[45] Date of Patent: Apr. 12, 1994

[54] METHOD FOR IMPROVING ENHANCED RECOVERY OF OIL USING SURFACTANT-STABILIZED FOAMS

[75] Inventors: Laurier L. Schramm; Conrad Ayasse; Karin Mannhardt; Jaromir Novosad, all of Calgary, Canada

[73] Assignee: Alberta Oil Sands Technology and Research Authority, Edmonton, Canada

[21] Appl. No.: 783,961

[22] Filed: Oct. 29, 1991

Related U.S. Application Data

[62] Division of Ser. No. 459,460, Jan. 2, 1990, Pat. No. 5,060,727.

[51] Int. Cl.⁵ ............................................. G01N 13/00
[52] U.S. Cl. ................................ 73/53.01; 73/60.11; 73/64.55
[58] Field of Search ............... 73/60.11, 61.41, 61.43, 73/64.48, 64.55, 53.01, 64.56; 422/58, 68.1, 256; 166/252; 356/440, 246

[56] References Cited

U.S. PATENT DOCUMENTS

| | | | |
|---|---|---|---|
| 4,084,426 | 4/1978 | Gales | 73/60.11 |
| 4,161,217 | 7/1979 | Dilgren et al. | 166/272 |
| 4,380,266 | 4/1983 | Wellington | 166/252 |
| 4,589,276 | 5/1986 | Djabbarah | 73/60.11 |
| 4,597,442 | 7/1986 | Dilgren et al. | 166/272 |
| 4,601,336 | 7/1986 | Dilgren et al. | 73/60.11 |
| 4,694,906 | 9/1987 | Hutchins et al. | 166/294 |
| 4,706,752 | 10/1987 | Holm | 166/273 |
| 4,768,592 | 9/1988 | Perkins | 166/275 |
| 4,836,281 | 6/1989 | Robin et al. | 166/273 |
| 4,856,589 | 8/1989 | Kuhlman et al. | 166/273 |

*Primary Examiner*—Hezron E. Williams
*Assistant Examiner*—Michael Brook
*Attorney, Agent, or Firm*—Millen, White, Zelano & Branigan

[57] ABSTRACT

A process is provided for enhancing the recovery of oil in a subterranean formation. The process involves injecting a surfactant-containing foam having oil-imbibing and transporting properties. A foam having such properties is selected either by determination of the lamella number or by micro-visualization techniques.

7 Claims, 5 Drawing Sheets

A: SURFACTANT DELIVERY
B: NITROGEN GAS DELIVERY
C: NON-RETURN VALVE
D: FOAM GENERATOR
E: PRESSURE MEASUREMENT
F: OIL/AQUEOUS SEPARATOR

METHOD FOR IMPROVING ENHANCED RECOVERY OF OIL USING SURFACTANT-STABILIZED FOAMS

This is a division of application Ser. No. 07/459,460, filed Jan. 2, 1990, now U.S. Pat. No. 5,060,727.

FIELD OF THE INVENTION

The present invention relates to a process for the enhanced recovery of oil from a subterranean oil-bearing formation.

BACKGROUND OF THE INVENTION

In the recovery of oil from a subterranean oil-bearing formation only between about ten to fifty percent of the oil in place is recoverable using combined primary and secondary production modes. As a result, tertiary or enhanced oil recovery processes have been developed. Such processes include thermal processes exemplary of which are steam flooding and in-situ combustion, chemical flooding techniques and gaseous displacement drives. The gases used may include steam, carbon dioxide or hydrocarbons.

However, several problems occur when a gas phase is used as the displacing medium. First, fingering of the gas phase into the oil will degrade the uniform displacement front with concomitant reduction in oil recovery. This is a result of the adverse mobility ratio between the displacing gas and the oil. Secondly, the density difference between the gas and oil phase will cause gravity override wherein the gas will tend to move upwardly, sweeping only the upper portion of the oil-bearing zone. Finally, reservoir heterogeneities and zones of relatively well swept (i.e. low oil) rock can cause the displacement fluid to channel through the oil-bearing zones. All of these phenomena act to reduce the amount of oil recovered.

The use of surfactant-stabilized foams comprises a relatively new technology for circonventing these problems.

The foam, having a viscosity greater than the displacing medium, will preferentially accumulate in the well-swept and/or higher permeability zones of the formation. The displacing medium is thus forced to move into the unswept or underswept areas of the formation. It is from these latter areas that the additional oil is recovered. However, when a foam is used to fill a low oil content area of the reservoir, the oil contained therein is, for all practical purposes, lost. This is because the foam functions to divert the displacement fluid from such areas.

The selection of suitable foam-forming surfactants which produce foams having the necessary stability to collapse and viscosity is crucial. Such properties as solubility, surface tension and bulk foam stability must be taken into consideration. Typical tests for the evaluation of surfactants would include solubility tests in the salinity, and temperature environment of the particular reservoir, bulk foam tests to ensure the stability of the foam to collapse, and permeability or pressure drop measurements made in packed sand beds or cores containing injected foam. U.S. Pat. Nos. 4,589,276 to Djabbarah and 4,601,336 to Dilgren et. al. cover some of these tests.

Recent studies have indicated that many foams are destroyed upon being brought into contact with an oil phase. It is desirable that the foam not collapse upon contact with the residual oil in the swept portions of the reservoir, nor block unswept portions thereof.

The classical description of foam oil interactions has been outlined by S. Ross, J. Phys. Colloid Chem. 54(3) 429–436 (1950). Ross sets forth that foam stability in the presence of oil can be described from thermodynamics in terms of the Spreading and Entering Coefficients S and E respectively. These coefficients are defined as follows:

$$S = \gamma_F{}^o - \gamma_{OF} - \gamma_O{}^o$$

wherein
$\gamma_F{}^o$ is the foaming solution surface tension;
$\gamma_{OF}$ is the foaming solution-oil interfacial tension; and
$\gamma_O{}^o$ is the surface tension of the oil.

$$E = \gamma_F{}^o + \gamma_{OF} - o^o$$

wherein
$\gamma_F{}^o$ $\gamma_{OF}$ and $\gamma_O{}^o$ are as defined supra.

Based on these coefficients, one can predict that three types of oil-foam interactions could take place. First, (Type A) an oil will neither spread over nor enter the surface of foam lamellae when E and S are less than zero. Secondly, (Type B) oil will enter but not spread over the surface of foam lamellae when E is greater than zero but S is less than zero. Thirdly, (Type C) oil will enter the surface of foam lamellae and then spread over the lamellae surfaces if both E and S are greater than zero. This latter behaviour, typically, will destabilize the foam. However, experimental results have not borne out these predictions. Furthermore, the theory was developed assuming that the oil droplets are readily imbibed into the foam lamellae. Again however, experimental results show that some foams, particularly those of type A supra do not readily imbibe oil.

There exists, therefore, a need to distinguish between foams which are stable to oil but do not significantly imbibe oil, as in type A supra, foams which are stable to oil and do imbibe oil as in the second type above and finally, foams that are unstable to oil as in the third predicted type.

SUMMARY OF THE INVENTION

In accordance with the present invention, it has been discovered that foams having the properties of being stable in the presence of an oil phase or additionally being functional to imbibe and transport the oil phase can be realized.

Furthermore, it has been found that each foam-forming surfactant providing these properties can be determined by one of two methods.

The first method relies on the discovery that there exists a correlation between foam stability and oil imbibing properties and a coefficient referred to herein as the Lamella Number (L). More specifically, the lamella number L is defined as:

$$L = \frac{\gamma_F{}^o r_0}{\gamma_{OF} r_p}$$

wherein
$\gamma_F{}^o$ is the foaming solution surface tension;
$r_0$ is the radius of an emulsified drop;
$\gamma_{OF}$ is the foaming solution-oil interfacial tension; and
$r_p$ is the radius of a foam lamella Plateau border where it initially contacts the oil. The plateau border refers to the part of a foam lamella that has curved surfaces. Plateau borders occur where a foam lamella meets either another foam lamella, or a surface of another material such as oil or solid.

It is to be noted that, because oil imbibition is of interest, $r_o$ can be equated to one-half the thickness of a foam lamella.

Thus, when L is greater than one, emulsification and imbibition of oil into a foam will occur. If L is substantially equal to, or greater than about seven, the imbibition of large amounts of small droplets will result in foam destruction. Thus, a surfactant generating a foam "which is stable to collapse in the presence of an oil phase would be one having a lamella number less than seven. Additionally a foam having the stability and which will imbibe and transport an oil phase", would be one having a lamella number ranging between one and seven.

The second method involves using direct observation of foam behaviour using micro-visualization apparatus and comparing the observed behaviour with known models so as to categorize said surfactants functional to generate a foam which is stable to collapse in the presence of an oil phase or which additionally are capable of both imbibing and transporting the oil phase.

In one broad aspect, the invention provides a method for testing whether a surfactant-containing foam is stable against collapse in the presence of an oil phase in a subterranean formation, comprising: determining the lamella number, L, of the foam, by:
(a) determining the surface tension of the foam, $\gamma^0_F$;
(b) contacting the foam with an oil phase;
(c) determining the radius of a foam lamella plateau border where it initially contacts the oil phases $r_p$;
(d) determining the radius of an emulsified drop of oil in the foam, $r_0$;
(e) determining the interfacial tension between the foam and the oil phase, $\gamma_{OF}$; and
(f) calculating L from the mathematical model $$L = \frac{\gamma_F^0 r_0}{\gamma_{OF} r_p}$$

and
determining whether the L of the foam is less than seven, said range being indicative of foams which are stable against collapse in the presence of an oil phase.

In another broad aspect, the invention provides an apparatus for use in selecting a surfactant-containing foam which is stable against collapse in the presence of an oil phase in a subterranean formation, comprising:
a transparent cell;
a first channel providing for the flow of foam lamella through the cell; and
a second channel providing for the flow of oil into the cell, said second channel intersecting and terminating at said first channel.

DESCRIPTION OF THE PREFERRED EMBODIMENT

Having reference to the accompanying drawings there is provided in a first aspect a process for enhancing the recovery of oil in a subterranean formation which involves injecting a foam having oil imbibing and transporting properties.

The foam exhibiting such properties is selected by either of the two methods described herebelow.

Determination of the Lamella Number

There exists a correlation between foam stability and oil imbibing properties and a coefficient referred to herein as the Lamella Number (L). More specifically, the lamella number L is defined as:

$$L = \frac{\gamma_F^0 r_0}{\gamma_{OF} r_p}$$

wherein
$\gamma_F^0$ is the foaming solution surface tension;
$r_0$ is the radius of an emulsified drop;
$\gamma_{OF}$ is the foaming solution-oil interfacial tension; and
$r_p$ is the radius of a foam lamella plateau border where it initially contacts the oil.

It is to be noted, that because oil imbibition is of interest, $r_o$ can be equated to one-half the thickness of a foam lamella.

The surface tension can be determined using the standard du Nouy ring technique as is described in standard textbooks of colloid chemistry.

The interfacial tensions between the oil and the foam forming solution may be measured using the spinning drop tensiometer as described by J. L. Cayias, R. S. Schechter, and W. H. Wade in Adsorption at Interfaces, ACS Symp. Ser., No. 8, 234–247 (1975).

The radius of an emulsified drop ($r_o$) was determined using the micro-visualization apparatus described below. Similarly, the radius of a foam lamella Plateau border where it initially contacts the oil ($r_p$) was determined using the same apparatus. However, the ratio of the radius $r_0/r_p$ was measured for a number of surfactant stabilized foams of 95% quality and found to have a constant value of about 0.15. By 95% quality is meant 95 volume percent gas and 5 volume percent aqueous solution. Thus a useful approximation is to use a value of about 0.15. In this case the micro-visualization apparatus is not needed and only the surface and interfacial tensions have to be measured, which can be done using readily available apparatus.

It is to be noted that the lamella number is the ratio of two forces namely a) the capillary suction force exerted by the foam lamellae causing oil to be drawn up into the lamellae where it is pinched off into droplets and b) the resisting force provided by the interfacial tension of the oil which counteracts the capillary suction force.

Micro-visualization Determination

Figure 1:
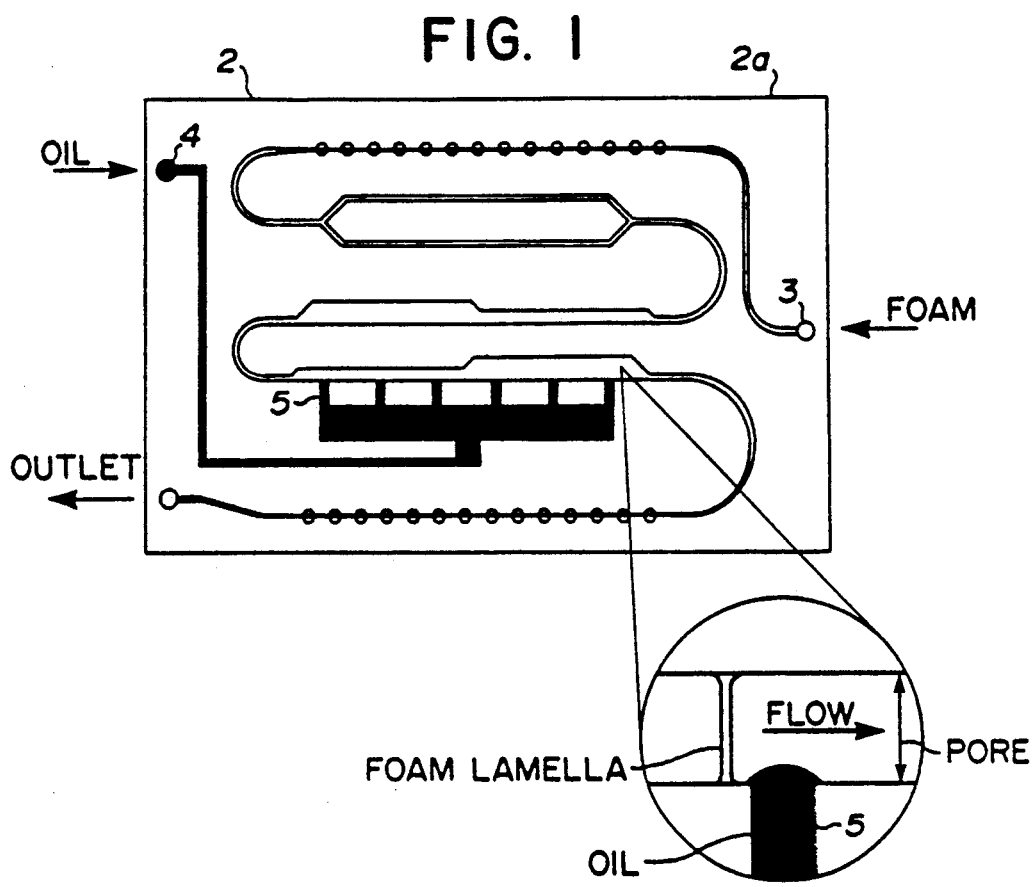
FIG. 1 is a schematic showing the micro-visualization apparatus used in one aspect of the practice of the present invention.
Figure 2:
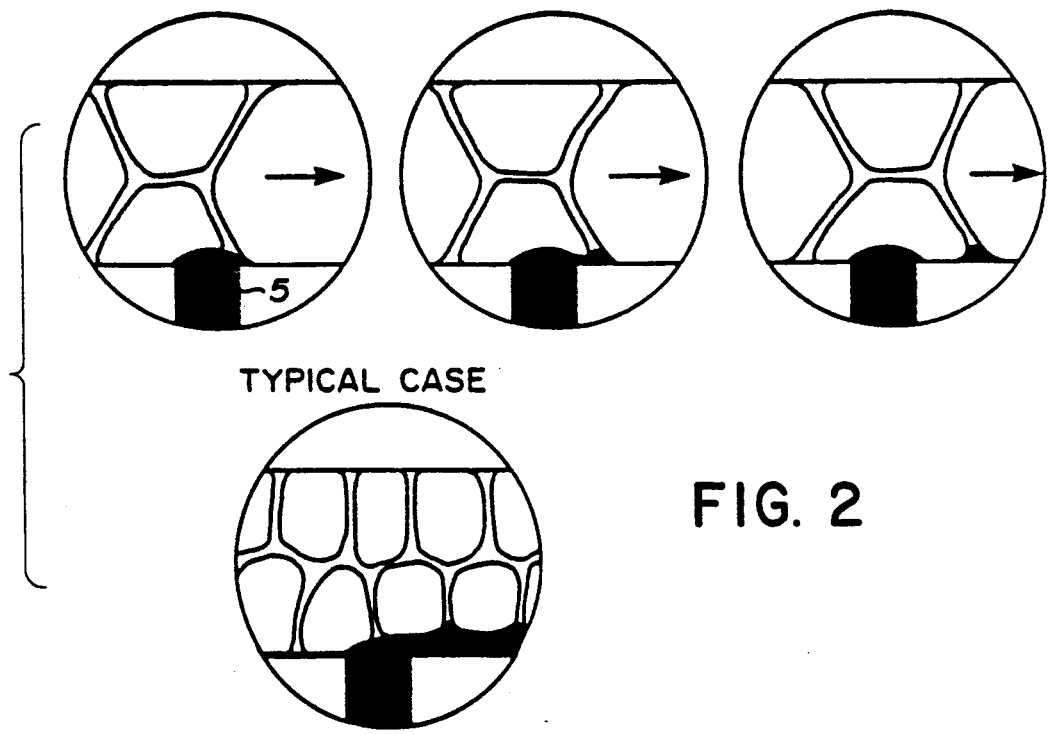
FIG. 2 is an illustrative representation of a Type A foam which upon contact with an oil phase shows little interaction therewith.
Figure 3:
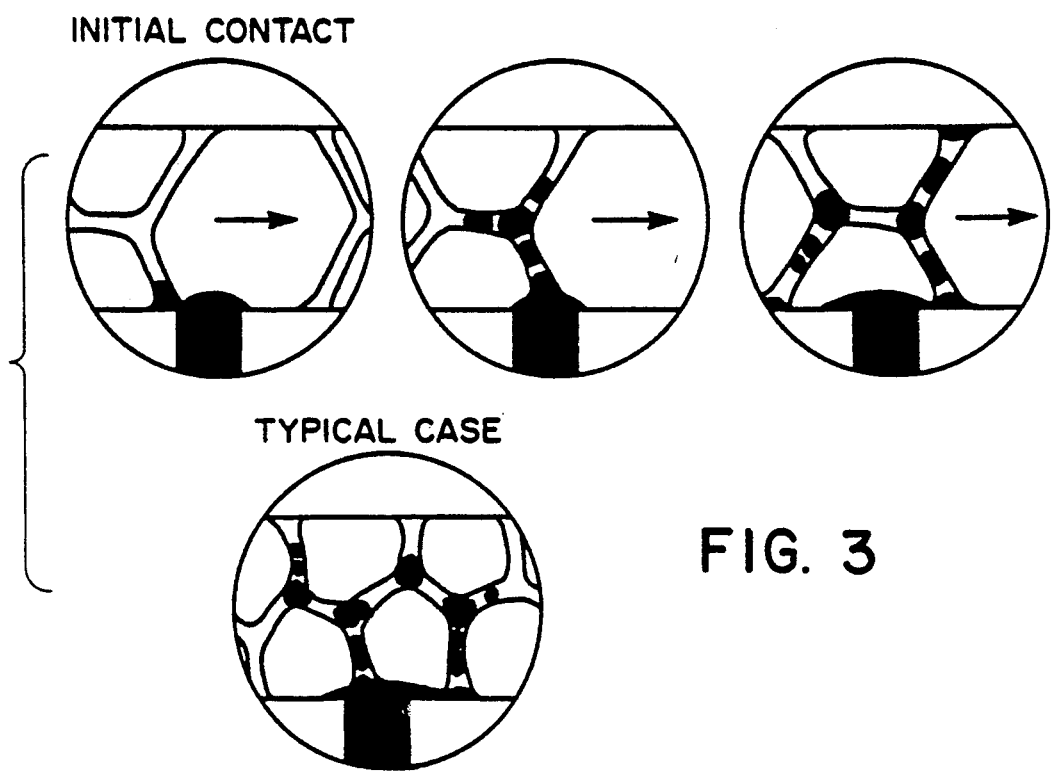
FIG. 3 is an illustrative representation of a Type B foam which upon contact with an oil phase has the capability of imbibing and transporting said oil.
Figure 4:
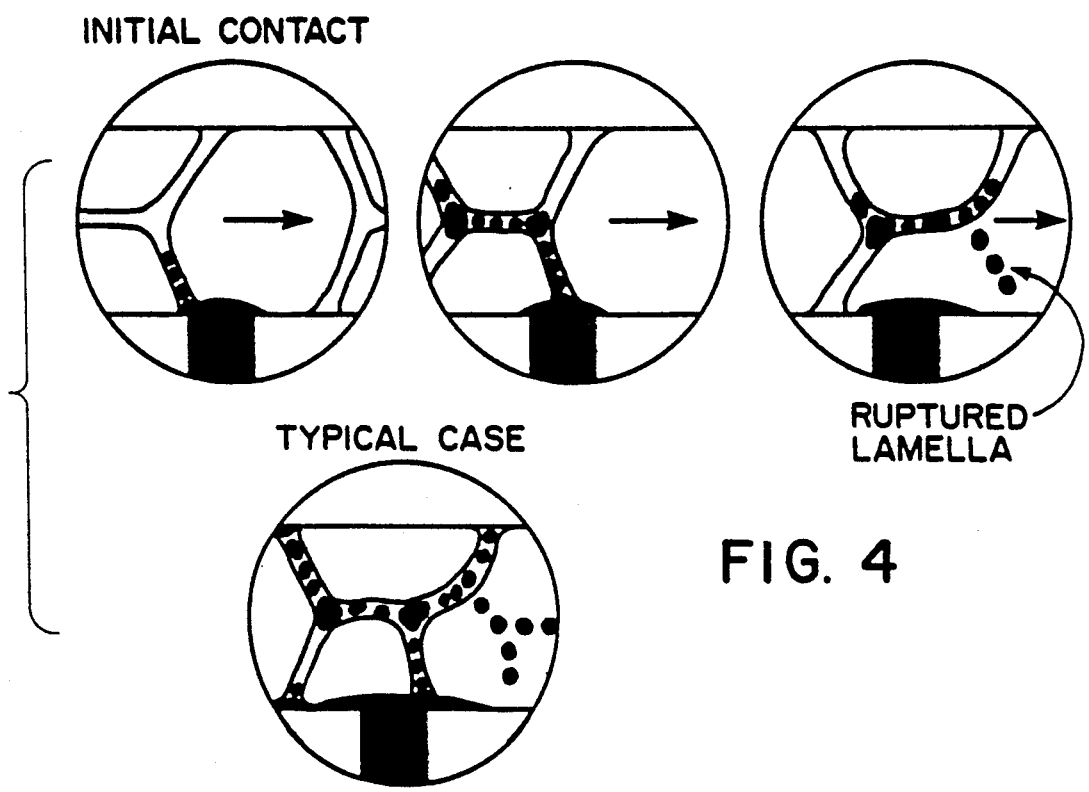
FIG. 4 is an illustrative representation of a Type C foam which upon contact with an oil phase is destroyed by rupturing of its lamella.

Having particular reference to FIG. 1, the microvisualization apparatus of the present invention utilizes a pair of glass plates 2. A flow pattern 3 is etched into one of the two glass plates 2a. A key feature of the flow pattern is that advancing foam lamellae and oil could be brought into contact in a controllable fashion. The etched pattern represented a model of a small part of the micro-structure in a porous medium. The typical pore areas ranged from 380-3000×55-65 μm. The plates 2 were placed together in a holder (not shown) adapted for observation in a conventional microscope (again, not shown). A first inlet part 3 was provided for the introduction of foam therein. A second inlet port 4 communicating with a series of divided inlet ports 5 was provided for introduction of the oil between the plates 2 and its subsequent contact with the foam.

The novel features of the flow network are (1) that separate injection and control of the flow of foam lamellae and of the oil are possible, and (2) that channels are provided such that flowing foam lamellae can be observed under two very important conditions as follows. First, the flow behaviour of foam lamellae can be observed in pores and throats in the absence of oil (upper pathways in FIG. 1). Secondly, the behaviour of the foam lamellae can be observed during their initial and subsequent encounters with oil in the region of the cell where the oil channels intersect the foam channels.

The microvisualization apparatus permits assessment of two properties: (1) the ability to imbibe and transport oil, which can be observed directly, and (2) the stability to breakage in the presence of the oil, which can be measured in the apparatus. The combination of these is assessed versus known models.

EXPERIMENTAL

The experimental results given in Table I herebelow show the interaction of various foams with David crude oil. The crude oil used was a well head sample produced from the Lloydminster sand, in the David field having a density of 0.9259 g/mL and viscosity of 207 mPa.s, both at 23.0° C.

TABLE I

| Surfactant (0.5% mass) Concentration | Brine Solution mass % | $\gamma_F^a$ mN/M | $\gamma_O^\sigma$ mN/m | $\gamma_{OF}$ mN/m | E mN/m | S mN/m | L | $f_b$ $s^{-1}$ | Foam Type |
|---|---|---|---|---|---|---|---|---|---|
| Fluorad FC-751 | 0.0 | 19.3 | 29.3 | 6.6 | −3.4 | −16.6 | 0.4 | 0.00 | A |
| Fluorad FC-751 | 2.1 | 19.0 | 29.3 | 7.0 | −3.3 | −17.3 | 0.4 | 0.00 | A |
| Dow XS84321.05 | 0.0 | 35.0 | 29.3 | 4.5 | 10.2 | 1.2 | 1.1 | 0.02 | B |
| Dow XS84321.05 | 2.1 | 32.2 | 29.3 | 1.2 | 4.1 | 1.7 | 3.9 | 0.02 | B |
| Stepanflo 60 | 0.0 | 29.2 | 29.3 | 2.5 | 2.4 | −2.6 | 1.7 | 0.02 | B |
| Varion CAS | 0.0 | 36.0 | 29.3 | 0.8 | 7.5 | 6.0 | 7.1 | 0.03 | C |
| Atlas CD-413 | 0.0 | 35.0 | 29.3 | 0.4 | 6.1 | 5.3 | 13.8 | 0.03 | C |
| Atlas CD-413 | 2.1 | 30.7 | 29.3 | 0.2 | 1.6 | 1.2 | 23.4 | 0.05 | C |

EXAMPLE II

The crude oil was a well head sample produced from the Judy Creek field, Beaverhill Lake pool having a density of 0.8296 g/mL and viscosity of 4.6 mPa.s, both at 23.0±0.5° C. Values obtained for the physical properties and $f_b$ are given in Table II herebelow.

Examples I and II show that for a range of oils and foams there is a correlation between the micro-visual method (combination of $f_b$ and Foam Type columns) and the first method (L column). Thus either method yields the same needed information.

TABLE II

| Surfactant 0.5% mass | Brine Conc. mass % | Foam Surface Tension mN/m | Oil Surface Tension mN/m | Initial IFT mN/m | E mN/m | S mN/m | L | $f_b$ $s^{-1}$ | Foam Type |
|---|---|---|---|---|---|---|---|---|---|
| Fluorad FC-751 | 0.0 | 19.3 | 24.3 | 4.7 | −0.3 | −9.7 | 0.60 | 0.002 | A |
|  | 2.1 | 19.0 | 24.3 | 5.2 | −0.1 | −10.5 | 0.53 | 0.000 | A |
| Mixture + | 2.1 | 30.6 | 24.3 | 0.66 | 7.0 | 5.6 | 6.7 | 0.020 | B |
| Na Dodecyl Sulfate | 0.0 | 38.3 | 24.3 | 5.1 | 19.1 | 8.9 | 1.1 | 0.013 | B |
| Dow XS84321.05 | 0.0 | 35.0 | 24.3 | 2.3 | 13.0 | 8.4 | 2.2 | 0.018 | B |
|  | 2.1 | 32.2 | 24.3 | 0.62 | 8.5 | 7.3 | 7.6 | 0.041 | C |
| Varion CAS | 0.0 | 36.0 | 24.3 | 0.57 | 12.3 | 11.1 | 9.2 | 0.042 | C |
|  | 2.1 | 35.7 | 24.3 | 0.50 | 11.9 | 10.9 | 10.4 | 0.039 | C |
| Atlas CD-413 | 0.0 | 35.0 | 24.3 | 0.51 | 11.2 | 10.2 | 10.0 | 0.039 | C |
|  | 2.1 | 30.7 | 24.3 | 0.41 | 6.8 | 6.0 | 10.9 | 0.037 | C |

+ Mixture of 0.49% Varion CAS plus 0.01% Fluorad FC-751 surfactants.

EXAMPLE III

Using the same light crude oil as in Example II, the invention was tested in low pressure ambient temperature corefloods.

Figure 5:
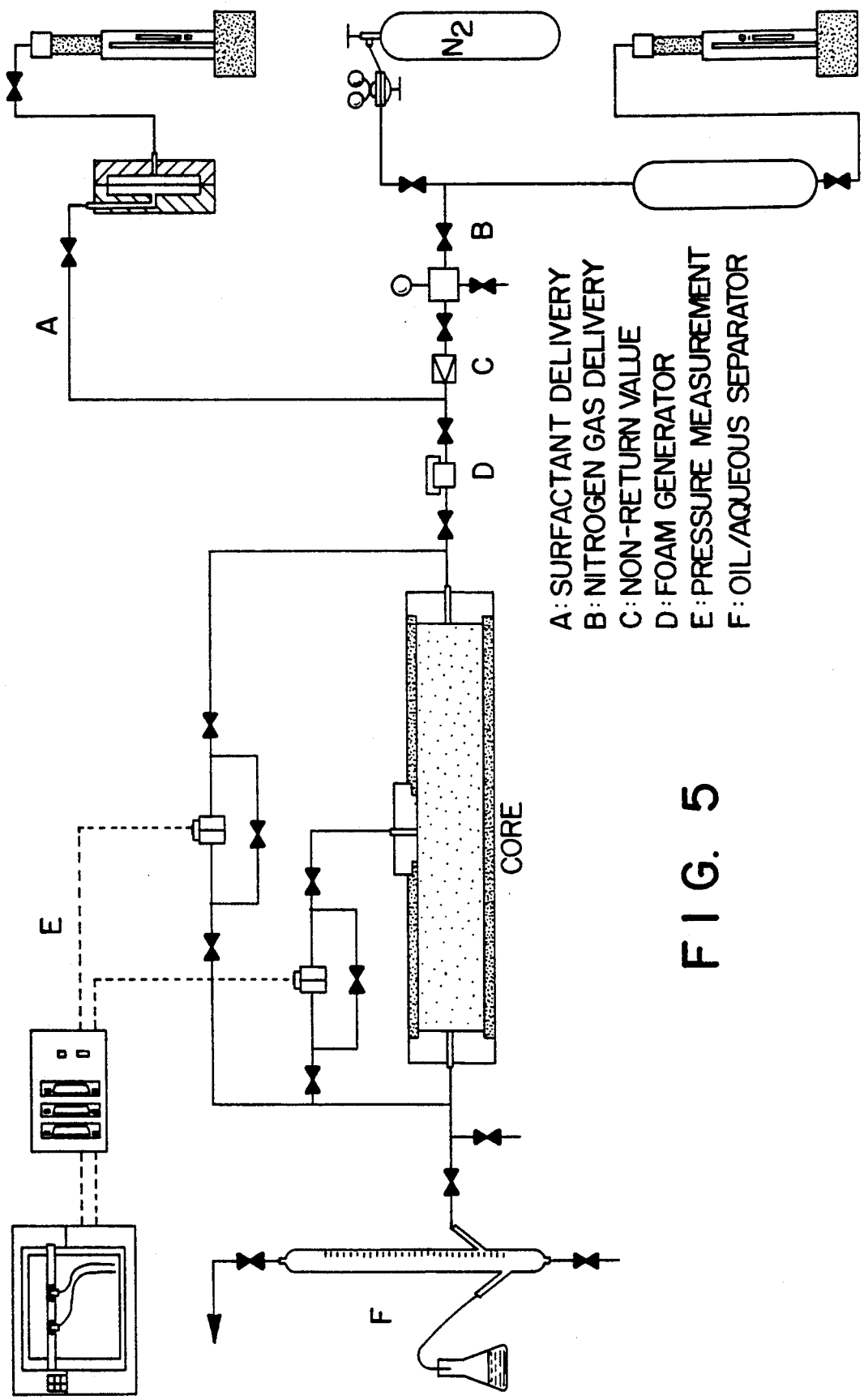
FIG. 5 is a schematic showing the core flood test apparatus.

Method. The porous medium used was Berea sandstone cut into 2.5×2.5×20 cm blocks that had been wrapped in fiberglass tape and cast in epoxy resin. These blocks had pore volumes of about 30 mL and absolute air permeabilities of about 630 to 1040 md. Although the Berea cores were selected to have similar properties there is some unavoidable variation. The cores were flooded using the coreflooding apparatus illustrated in FIG. 5. Foam was pregenerated by passing gas and surfactant solution through a 7 micrometer in-line filter. Oil and aqueous phase productions were measured by separating them in a glass buret and drawing off the aqueous phase to a separate container. The tests were conducted at constant imposed rates of gas and liquid injection. For each experiment a fresh epoxy-coated sandstone core was prepared and saturated with brine by imbibition. Subsequently, the core was flooded as follows:

1. Brine was injected to saturate the core and measure the absolute permeability to brine.
2. Oil was injected into the core, displacing brine, until the residual water saturation was attained. The first few pore volumes were injected from the top down with the core in a vertical orientation and at a very low rate (2 mL/hr), subsequently 6-8 pore volumes (PV) were injected with the core horizontal, at a high rate (72 mL/hr).
3. The core was mounted in the apparatus and brineflooded at a rate of 2-18 mL/hr (linear superficial velocity=0.3-3 m/day), until the (unchanging) residual oil saturation was obtained, usually after 6-8 PV of brine.
4. Gas and brine were injected simultaneously at predetermined rates in order to measure the pressure drop base lines.
5. Surfactant solution was injected for surfactant pre-equilibration (to satisfy the adsorption requirement of the core and to determine any oil recovery due to surfactant alone); 6-7 PV were injected in 24-48 hours at a rate of 2-18 mL/hr.
6. Foam was pregenerated in the in-line filter and injected into the core at an initial pressure smaller than the expected pseudosteady-state injection pressure.

To assure the repeatability of the tests, foam flooding was carried out in a series where rate and foam quality were changed in such a way that the pressure drop was always increasing. Each surfactant was tested using total volumetric rates of about 19 mL/hr (3 m/day) and foam qualities of about 96%. Sufficient time was allowed to attain the pseudosteady-state, an average duration was 2 weeks of continuous operation.

Figure 6:
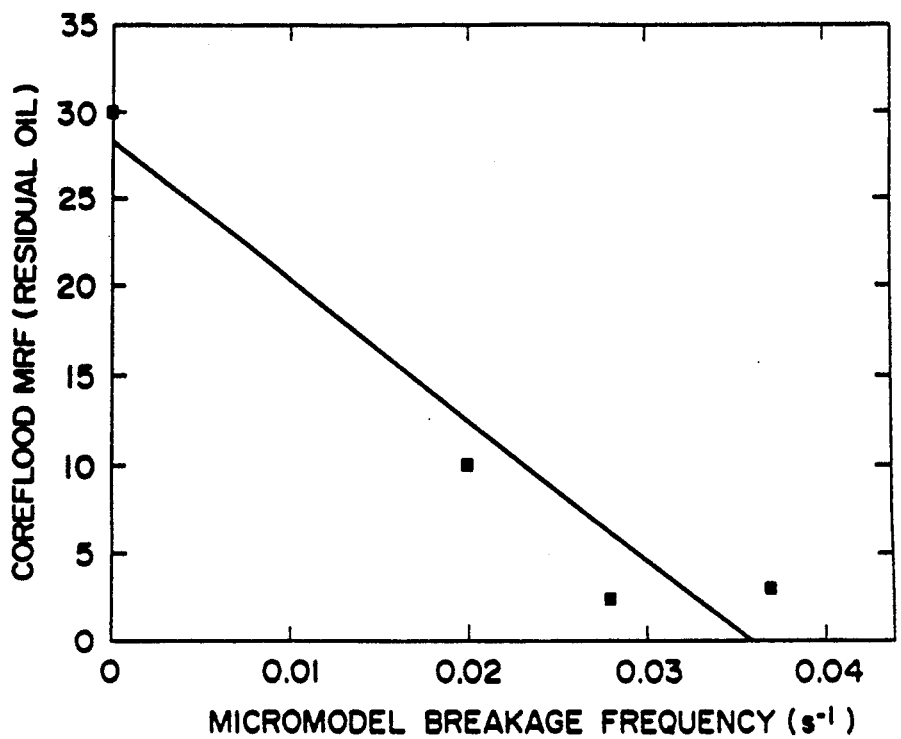
FIG. 6 is a plot of coreflood MRF (defined below) versus micromodel breakage frequency to illustrate the correlation between coreflood MRF (Residual Oil) and micromodel foam stabilities.
Figure 7:
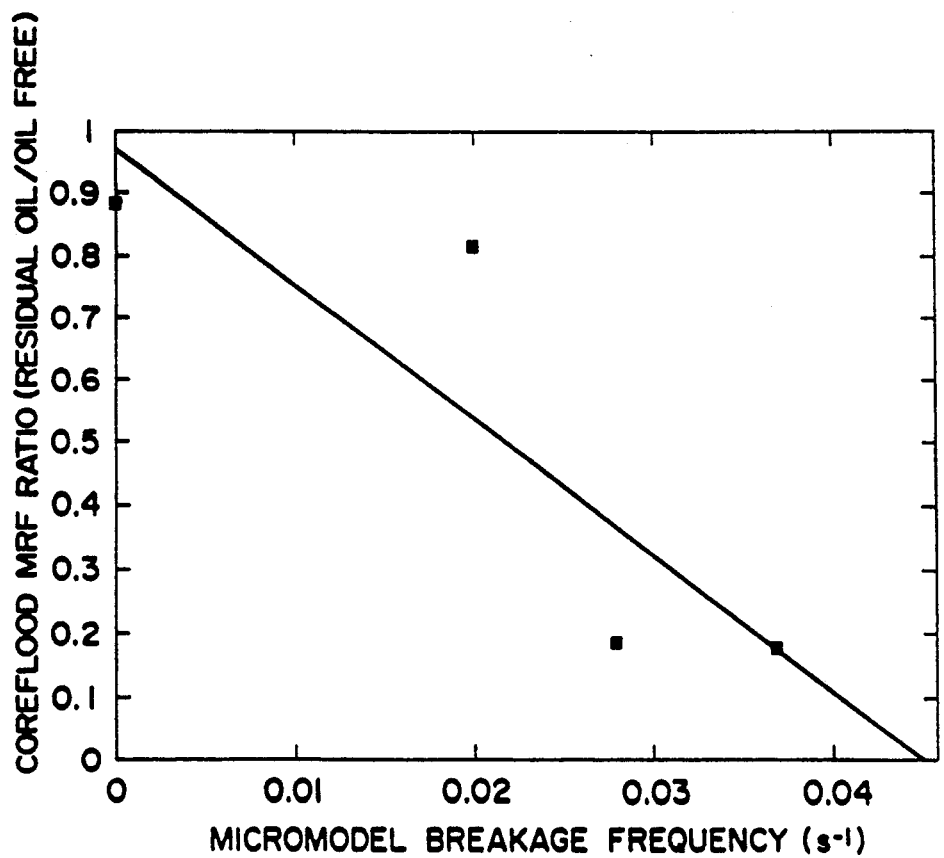
FIG. 7 is a plot of coreflood MRF ratio (Residual oil to MRF oil-free) versus micromodel breakage frequency to illustrate the correlation between normalized coreflood, MRF, MRF (Residual Oil/MRF (Oil-free) and micromodel foam stabilities.
Figure 8:
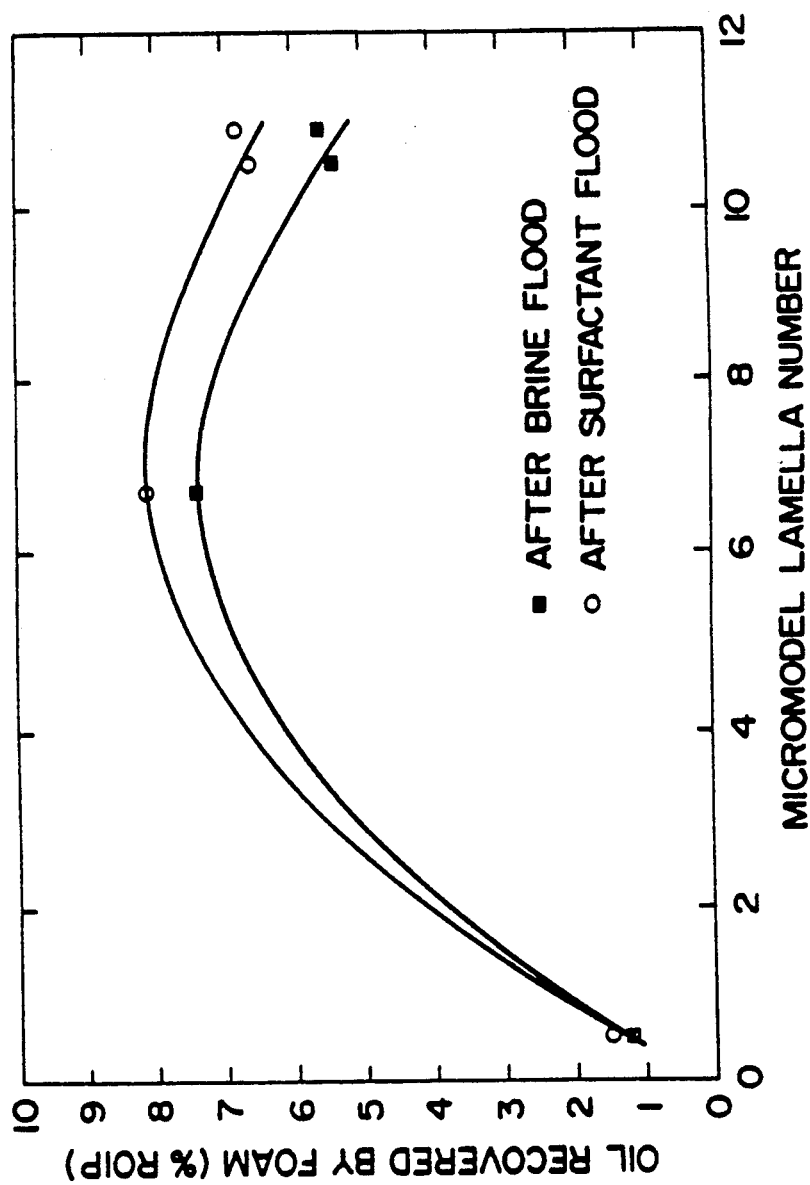
FIG. 8 is a graph of the oil recovered from corefloods by the foam versus the micromodel lamella number to illustrate the correlation therebetween.

From the data in Example III, foams predicted to yield types A, B and C behaviour were selected for coreflood testing. The efficiency of the selected foams with regard to their capacity to improve volumetric sweep efficiency in porous media was evaluated based on mobility reduction factor (MRF): a ratio of the pseudo-steady state pressure drops across a core with foam and with only gas and brine flowing at rates equivalent to those in the foam. FIG. 6 shows the MRF's measured for foam in the presence of residual oil versus micromodel breakage frequencies in the presence of oil. Since each foam did not behave identically in the oil-free cores, that is the oil-free core MRF's were not all the same, the ratio of residual oil MRF to oil-free core MRF for each foam is plotted in FIG. 7. These results establish the correlation between micromodel and coreflood foam stabilities to oil.

EXAMPLE IV

The final example illustrates the use of the invention in a secondary flood application using the surfactant found to yield type B behaviour in Example II and used in a tertiary foam flood in Example III. In a separate experiment a Berea core was brine and oil saturated as in Example III, but instead of flooding with a sequence of brine (waterflooding), then gas/brine, surfactant solution and foam, in this case it was flooded directly with foam. Thus the foam was injected as a secondary recovery process. The results are shown in Table III herebelow.

TABLE III

| Foam Injection Mode | Initial Oil Saturation (% PV) | Residual Oil Saturations | | Total Oil Recovery (% OOIP) |
|---|---|---|---|---|
| | | After Brine (% PV) | After Foam (% PV) | |
| Brine only | 63 | 28 | n.a. | 56 |
| Tertiary Foam | 63 | 28 | 23 | 63 |
| Secondary Foam | 63 | n.a. | 20 | 68 | n.a.: not applicable.
% PV: percent of pore volume
% OOIP: percent of original oil in place Examples III and IV show that having selected the stable oil-imbibing and transporting type of foam using the methods of the present invention more efficient enhanced and secondary oil recovery processes are achieved. This is shown for enhanced recovery by the optimal incremental oil recovery (i.e., above and beyond that from brine flooding and surfactant solution flooding) of the Type B foam compared with the poorer recoveries for the Types A and C foams. The Type B foam matches both of our selection method criteria (micro-visual criteria of behaviour and $f_b$, and the correlation: L=6.7 is between 1 and 7). Example IV shows that the Type B foam is not only optimal for enhanced oil recovery but in a secondary oil process the total oil recovery is even better. The extra oil recoveries are due to the oil-imbibing and transporting property of the Type B foams selected from by the present methods.

The embodiments of the invention in which an exclusive property or privilege is claimed are defined as follows:

1. A method for selecting a surfactant for use in a surfactant-containing foam which is stable against collapse in the presence of an oil phase in a subterranean formation, comprising:

(i) forming a surfactant-containing foam with a test surfactant;

(ii) determining the lamella number, L, of the foam, by:

(a) determining the surface tension of the foam, $\gamma_F^O$;

(b) contacting the foam with an oil phase;

(c) determining the radius of a foam lamella plateau border where it initially contacts the oil phases, $r_p$;

(d) determining the radius of an emulsified drop of oil in the foam, $r_O$;

(e) determining the interfacial tension between the foam and the oil phase, $\gamma_{OF}$; and (f) calculating L from the mathematical model $$L = \frac{\gamma_F^0 \, r_O}{\gamma_{OF} \, r_p} ;$$

(iii) determining whether the L of the foam is less than 7, said range being indicative of foams which are stable against collapse in the presence of an oil phase; and (iv) selecting the surfactant if it has a value of L less than 7 for use in a surfactant-containing foam which is stable against collapse in the presence of an oil phase in a subterranean formation.

2. The method as set forth in claim 1, which further comprises:
   determining in step (iii) whether the L of the foam lies inside or outside the range of 1 to 7, said range being indicative of foams which are functional to both imbibe and transport an oil phase, and
   selecting the surfactant if it has an L value inside the range of 1 to 7 for use in a surfactant foam capable of both imbibing and transporting an oil phase in a subterranean formula.

3. A method for selecting a surfactant for use in a surfactant-containing foam which is stable against collapse in the presence of an oil phase in a subterranean formation, comprising:
   (i) forming a surfactant-containing foam with a test surfactant;
   (ii) determining the lamella number, L, of the foam by:
      (a) determining the surface tension of the foam, $\gamma_F^O$;
      (b) contacting the foam with an oil phase;
      (c) determining the interfacial tension between the foam and the oil phase, $\gamma_{OF}$; and
      (f) calculating L from the mathematical model $$L = 0.15 \frac{\gamma_F^O r_0}{\gamma_{OF} r_p} ;$$

(iii) determining whether the L of the foam is less than 7, said range being indicative of foams which are stable against collapse in the presence of an oil phase; and
   (iv) selecting the surfactant of this a value of L less than 7 for use in a surfactant-containing foam which is stable against collapse in the presence of an oil phase in a subterranean formation.

4. The method as set forth in claim 3, which further comprises:
   determining in step (iii) whether the L of the foam lies inside or outside the range of 1 to 7, said range being indicative of foams which are functional to both imbibe and transport an oil phase, and
   selecting the surfactant if it has an L value inside the range of 1 to 7 for use in a surfactant foam capable of both imbibing and transporting an oil phase in a subterranean formula.

5. An apparatus for use in selecting a surfactant-containing foam which is stable against collapse in the presence of an oil phase in a subterranean formation, comprising:
   a transparent cell;
   a first channel providing for the flow of foam lamella through the cell; and
   a second channel providing for the flow of oil into the cell, said second channel intersecting and terminating at said first channel.

6. The apparatus as set forth in claim 5, wherein said first channel extends through the cell between spaced apart foam inlet and foam outlet ports, said second channel extends into the cell from an oil inlet port, and said second channel is divided to intersect said first channel at a plurality of locations.

7. The apparatus as set forth in claim 6, wherein the cell is formed by a pair of glass plates, said first and second channels being etched in the surface of at least one plate.

* * * * *